United States Patent
Kim

(10) Patent No.: US 8,907,127 B2
(45) Date of Patent: Dec. 9, 2014

(54) PREPARATION METHOD OF 4-AMINOMETHYLBENZOIC ACID

(75) Inventor: Woo Sun Kim, Seoul (KR)

(73) Assignees: NAF Co Ltd, Daejeon (KR); SK Petrochemical Co Ltd, Ulsan (KR)

(*) Notice: Subject to any disclaimer, the term of this patent is extended or adjusted under 35 U.S.C. 154(b) by 42 days.

(21) Appl. No.: 13/522,465

(22) PCT Filed: Dec. 9, 2010

(86) PCT No.: PCT/KR2010/008774
§ 371 (c)(1),
(2), (4) Date: Jul. 16, 2012

(87) PCT Pub. No.: WO2011/087211
PCT Pub. Date: Jul. 21, 2011

(65) Prior Publication Data
US 2012/0296114 A1 Nov. 22, 2012

(30) Foreign Application Priority Data
Jan. 14, 2010 (KR) .......... 10-2010-0003577

(51) Int. Cl.
*C07C 227/04* (2006.01)
*C07C 249/08* (2006.01)
*B01J 21/18* (2006.01)
*B01J 23/40* (2006.01)
*B01J 23/44* (2006.01)
*B01J 23/75* (2006.01)

(52) U.S. Cl.
CPC .......... *C07C 227/04* (2013.01); *C07C 249/08* (2013.01); *B01J 21/18* (2013.01); *B01J 23/40* (2013.01); *B01J 23/44* (2013.01); *B01J 23/75* (2013.01)
USPC .......................................... 562/458

(58) Field of Classification Search
None
See application file for complete search history.

(56) References Cited

U.S. PATENT DOCUMENTS 4,973,746 A    11/1990   Blackmon et al.

FOREIGN PATENT DOCUMENTS

| JP | 56-012350 | 2/1981 |
| JP | 57-053441 | 3/1982 |
| KR | 10-0814597 | 3/2008 |
| WO | 2008/114506 | 9/2008 |

OTHER PUBLICATIONS

International Search Report mailed Aug. 29, 2011 which issued in corresponding International Patent Application No. PCT/KR2010/008774 (5 pages).

*Primary Examiner* — Brandon Fetterolf
*Assistant Examiner* — Ana Z Muresan

(57) ABSTRACT

The present invention relates to a preparation method of 4-aminomethylbenzoic acid comprising the following steps: preparing 4-carboxylbenzaldehyde or an alkyl ester thereof (methyl 4-formyl benzoate); reacting the 4-carboxylbenzaldehyde or an alkyl ester thereof (methyl 4-formyl benzoate) with hydroxyamine to oximate the same; and contact reducing 4-carboxylbenzaldehyde oxime or an alkyl ester oxime thereof obtained by the oximation, through hydrogen in a sodium hydroxide aqueous solution. Since methyl 4-hydroxyiminomethylbenzoate is reacted as a raw material in the presence of an alkali, hydrogen of a relatively low pressure can be used and a purification process is also simple, thereby enabling preparation of 4-aminomethylbenzoic acid with a low cost and high yield.

9 Claims, No Drawings

PREPARATION METHOD OF 4-AMINOMETHYLBENZOIC ACID

CROSS-REFERENCE TO RELATED APPLICATIONS

This application is a U.S. national stage of International Patent Application No. PCT/KR2010/008774, filed Dec. 9, 2010, which claims priority to Korean Patent Application No. 10-2010-0003577 filed Jan. 14, 2010, the contents of which are each incorporated herein by reference in their entirety.

TECHNICAL FIELD

The present invention relates to a method of preparing 4-aminomethylbenzoic acid and salts thereof (hereinafter, which are referred to as "4-aminomethylbenzoic acid").

BACKGROUND ART 4-aminomethylbenzoic acid is utilized as a monomer for preparing polymers or as a raw material for producing antiplasmin agents and as a main ingredient of Cetraxate which is used to treat gastric ulcers.

Conventional methods of preparing 4-aminomethylbenzoic acid and its lower alkylester include subjecting methyl 4-formylbenzoate to catalytic reduction using a Raney nickel catalyst in the presence of ammonia or subjecting methyl 4-cyanobenzoic acid to catalytic reduction using a Raney nickel catalyst in the presence of ammonia or reacting methyl 4-chloromethylbenzoate with liquid ammonia.

However these methods are problematic because a large amount of secondary amine (amino-di-4-methylbenzoic acid) is generated and the yield is low, in particular 4-cyanobenzoic acid cannot be easily prepared or the yield is low. Furthermore, because the conventional methods cause high toxicity in terms of the properties and generate pollution, there are required methods of preparing 4-aminomethylbenzoic acid which are associated with low toxicity, no pollution, and high yield.

In order to solve the above problems, patent literature 1 discloses the preparation of 4-aminomethylbenzoic acid or 4-acetylaminobenzoic acid by subjecting 4-carboxybenzaldehyde or its alkylester to oximation thus obtaining an oxime which is then reduced using a nickel catalyst in the presence of ammonia or acetic anhydride.

However the method disclosed in patent literature 1 is problematic because catalytic reduction is carried out in the presence of ammonia or acetic anhydride, acetic acid, etc., and hydrogenation is conducted at a high pressure of 20 atm or more, and thus limitations are imposed on selecting the reactor that can be used, and the purification process is excessively expensive. Moreover, there is a high cost due to high pressure and the work is not consistent.

(Patent Literature 1) Patent Literature 1: Japanese Unexamined Patent Application Publication No. 1981-12350

DISCLOSURE

Technical Problem

Accordingly, an object of the present invention is to provide a novel method of preparing 4-aminomethylbenzoic acid, which is associated with low toxicity, no pollution, and high yield. In the present specification, 4-aminomethylbenzoic acid denotes 4-aminomethylbenzoic acid and salts thereof.

Technical Solution

In order to accomplish the above object, the present invention provides a method of preparing 4-aminomethylbenzoic acid, comprising preparing 4-carboxybenzaldehyde or alkylester thereof (methyl 4-formylbenzoate); reacting 4-carboxybenzaldehyde or alkylester thereof (methyl 4-formylbenzoate) with hydroxylamine, thus producing 4-carboxybenzaldehyde oxime or alkylester oxime thereof; and subjecting 4-carboxybenzaldehyde oxime or alkylester oxime thereof to catalytic reduction using hydrogen in a sodium hydroxide aqueous solution.

In an embodiment of the present invention, catalytic reduction may be performed using a catalyst.

In an embodiment of the present invention, the catalyst may include one or more selected from among palladium, platinum, rhodium, iridium, and nickel.

In an embodiment of the present invention, the catalyst may be a Pd/C catalyst in which an amount of Pd may be 1-15 wt %, particularly 1-10 wt %, and more particularly 5-10 wt %, based on the total weight of the catalyst.

In an embodiment of the present invention, catalytic reduction may be performed at a pressure of about 1-15 atm and at a temperature of about 30-50° C.

In an embodiment of the present invention, the method may further comprise concentrating and filtering the product, after carrying out the catalytic reduction.

In an embodiment of the present invention, catalytic reduction may be performed at a stirring rate of at least 1200 rpm, particularly about 1200-2500 rpm, more particularly about 1200-2000 rpm, and much more particularly 1200-1700 rpm.

In an embodiment of the present invention, 4-carboxybenzaldehyde oxime or alkylester oxime thereof may be contained in an amount of about 8-18 wt %, particularly about 12-18 wt %, and more particularly about 12-15 wt %, based on the total weight of the reactants.

In an embodiment of the present invention, the alkali may be added in an amount about 0.2-1.0 times, particularly about 0.5-1.0 times, and more particularly 0.7-1.0 times the weight of 4-carboxybenzaldehyde oxime or alkylester oxime thereof

Advantageous Effects

According to the preparation method of the present invention, methyl 4-hydroxyiminomethylbenzoate is reacted in the presence of an alkali, thus enabling the use of comparatively low hydrogen pressure, and also a purification process is simple, thus enabling 4-aminomethylbenzoic acid to be prepared in high yield at low cost.

BEST MODE

The objects, specific advantages and novel features of the present invention will be more fully understood from the following detailed description and preferred embodiments.

In a method of preparing 4-aminomethylbenzoic acid according to the present invention, 4-carboxybenzaldehyde or its alkylester (methyl 4-formylbenzoate) is first prepared. As such, an example of 4-carboxybenzaldehyde alkyl ester includes methyl 4-formylbenzoate as disclosed in Korean Patent No. 0814597, entitled Method of Separating Methyl 4-Formylbenzoate and Dimethylterephthalate.

4-carboxybenzaldehyde or its alkylester (methyl 4-formylbonzoate) is reacted with hydroxylamine thus forming an oxime product.

Also, 4-carboxybenzaldehyde oxime or its alkylester oxime obtained as above is subjected to catalytic reduction using hydrogen in the presence of an alkali, thus producing 4-aminomethylbenzoic acid.

Thus, the method of the present invention includes the reaction route of methyl 4-formylbenzoate (MFB)→methyl-4-hydroxyiminomethylbenzoate (MHB)→4-aminomethylbenzoic acid (AMBA). The reaction according to the present invention is a simplification over the conventional reaction route of MFB→MHB→4-hydroxyiminomethylbenzoic acid (HBA)→AMBA.

The reaction mechanism of the method of preparing AMBA according to the present invention is represented by Scheme 1.

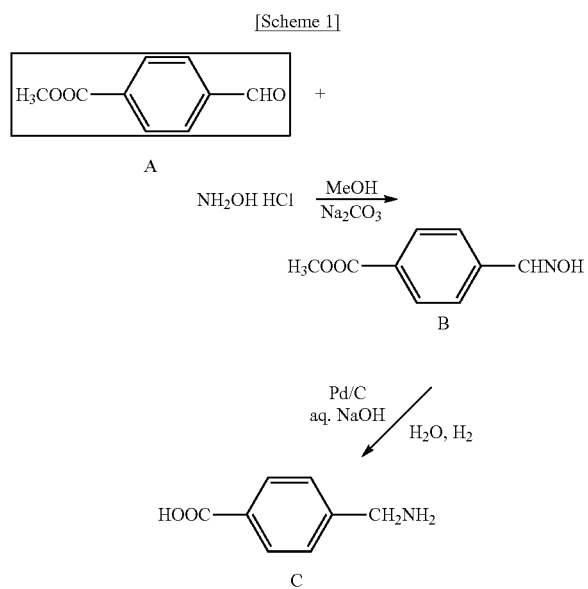

In Scheme 1, A is MFB, B is MHB, and C is AMBA.

The reaction yield of 4-aminomethylbenzoic acid obtained in the present invention may vary depending on the kind of alkali used. Particularly useful as the alkali is NaOH.

Also, catalytic reduction may be carried out using a catalyst, and the catalyst may include one or more selected from among palladium, platinum, rhodium, iridium, and nickel. Among these, particularly useful is Ni or palladium. More particularly a palladium catalyst is used, and the palladium catalyst is exemplified by a Pd/C catalyst, in which the amount of palladium metal is about 1-15 wt %, particularly about 1-10 wt %, and more particularly, about 5-10 wt %, based on the total weight of the catalyst.

The amount of added hydrogen may be easily determined by those skilled in the art so that it is adapted to each hydrogenation.

According to the method of the present invention, catalytic reduction is carried out at a pressure of about 1-15 kg/cm$^2$, particularly about 5-10 kg/cm$^2$. A typical AMBA preparation process is inefficient because hydrogenation is carried out at an excessively high pressure, for example, 20 kg/cm$^2$ or more. Whereas, in the case where AMBA is prepared using the method of the invention, hydrogenation is carried out at comparatively low pressure, remarkably increasing preparation efficiency.

The reaction temperature may be set in the range of room temperature (about 25° C.) to about 80° C., particularly about 30-50° C. If the reaction temperature is lower than room temperature, the reaction is slowed down and undesirably decreases the conversion to AMBA. In contrast, if the temperature is above 80° C., the amount of impurities is increased which also undesirably decreases the conversion to AMBA.

Furthermore, catalytic reduction may be performed at a stirring rate of at least about 1200 rpm, particularly about 1200-2500 rpm, more particularly about 1200-2000 rpm, and much more particularly about 1200-1700 rpm. If the stirring rate is less than 1200 rpm, the conversion to AMBA may decrease undesirably.

The method according to the present invention may further include concentrating and filtering the product, after carrying out the catalytic reduction. After completion of the reaction, the reaction product is filtered to remove the catalyst, and an acid or the like is added to the filtered solution to adjust the pH of the solution. As such, any acid such as hydrochloric acid, sulfuric acid, nitric acid, etc. may be added so long as it functions to adjust the pH, as known to those skilled in the art. Then, a drying process known to those skilled in the art at atmospheric pressure, i.e. vacuum drying, is performed to yield highly pure 4-aminomethylbenzoic acid.

Also in the method of preparing 4-aminomethylbenzoic acid according to the present invention, the reaction yield of 4-aminomethylbenzoic acid varies depending on the amount of NaOH added to the reaction solution. As the amount of NaOH increases, the amount of a dimer which is a by-product is decreased. Accordingly, NaOH may be added in an amount about 0.2-1.0 times, particularly 0.5-1.0 times the weight of methyl 4-hydroxyiminomethylbenzoate. If the amount of added NaOH is less than 0.2 times the weight of methyl 4-hydroxyiminomethylbenzoate, the conversion to AMBA is low and the amount of the dimer which is a by-product is increased. In contrast, if the amount of added NaOH is greater than 1.0 times the weight of methyl 4-hydroxyiminomethylbenzoate, the hydrogen solubility in the reaction solution may be lowered, so that the reduction reaction decreases, undesirably dropping the conversion to AMBA.

Also in the method of preparing 4-aminomethylbenzoic acid according to the present invention, the conversion to 4-aminomethylbenzoic acid varies depending on the reaction concentration of MHB (methyl 4-hydroxyiminomethylbenzoate).

As the concentration of MHB increases, the conversion to AMBA may decrease, as will be apparent from the following examples and comparative examples. The concentration of MHB is about 8-18 wt %, particularly about 9-17 wt %, and more particularly about 12-15 wt %, based on the total amount of the reactants. If the concentration of MHB is less than 8 wt %, the amount of finally obtainable AMBA may decrease undesirably. In contrast, if the concentration thereof exceeds 18 wt %, almost no MHB can be converted into AMBA even after the reaction, undesirably resulting in very low AMBA conversion.

A better understanding of the present invention may be obtained by means of the following preparative example and examples which are set forth to illustrate, but are not to be construed as limiting the present invention.

Preparative Example 1

200 parts by weight of methanol was added to 100 parts by weight of an admixture comprising, as by-products of a DMT preparation process, about 63 wt % of MFB, about 30 wt % of DMT, about 6 wt % of MPT, about 1 wt % of MBZ and a trace of other impurities, and the resulting mixture was stirred at 25° C. for 0.5 hr. After completion of the stirring, only DMT was left behind as a solid, and then filtered, thus recovering solid DMT. As such, the solid DMT was washed with methanol, yielding 29.5 g of DMT having 99.5% purity.

0.2 parts by weight of p-toluenesulfonic acid was added to the filtered solution, after which the solution was stirred for 2 hr, so that MFB was converted into 4-methoxycarbonylbenzaldehyde dimethylacetal. When the reaction product converted into 4-methoxycarbonylbenzaldehyde dimethylacetal was maintained at −2° C., the residual DMT precipitated as a solid, and the solution was then filtered at −2° C., thus recovering the residual DMT in solid form. The precipitated DMT was washed with methanol, yielding 2.1 g of DMT of 98.5% purity.

The methanol was recovered by distilling the above filtered solution, and 63 parts by weight of heptane and 63 parts by weight of water were added to the solution, and the resulting solution was stirred at 70° C. for 4 hr. After completion of the reaction, the reaction temperature was decreased to 25° C., and the reaction product was filtered, thus recovering solid MFB. The product MFB was dried at 50° C. and then recovered, yielding 40.5 g of MFB having 99.0% purity.

Example 1

886 g of methyl 4-formylbenzoate having 99.0% purity obtained in Preparative Example 1 was dissolved in 2000 g of methanol, after which reactants of 450 g (6.47 mole) of hydroxylamine hydrochloride in 650 g of water was added thereto and the reaction mixture was stirred at a stirring rate of 800 rpm at 25-35° C. for 2 hr. After methyl 4-formylbenzoate had been completely consumed from the reaction solution, a 30% sodium hydroxide aqueous solution was added to the reaction solution so that the pH of the solution was adjusted to 7.5-8.0 while performing vigorous stirring at a stirring rate of 1300 rpm, followed by filtering the solution. Drying was performed at 80° C. under atmospheric pressure for 4 hr, affording 962 g (yield 99.5%) of methyl 4-hydroxyiminomethylbenzoate having 99.0% purity.

310 g of methyl 4-hydroxyiminomethylbenzoate obtained as above, 3000 g of water, 168.5 g of sodium hydroxide and 22.5 g of 5 wt % Pd/C (wet 50% water) were placed in a 4 L autoclave, after which the reaction was carried out under conditions of a hydrogen pressure of 10 kg/cm$^2$, room temperature, a stirring rate of 1500 rpm, and a time of 3 hr. After the catalyst was removed, 452 g of conc. hydrochloric acid was added so that the solution was neutralized to pH 7, and water was then removed to concentrate the solution.

Subsequently, the concentrated solution was filtered and dried, thus obtaining 245 g (yield 93.5%) of 4-aminomethylbenzoic acid having 99.9% purity. As such, the melting point was 351.3-352.5° C.

Example 2

886 g of methyl 4-formylbenzoate having 99.0% purity obtained in Preparative Example 1 was dissolved in 2000 g of methanol, after which reactants of 450 g (6.47 mole) of hydroxylamine hydrochloride in 650 g of water was added thereto and the reaction mixture was stirred at a stirring rate of 800 rpm at 25-35° C. for 2 hr. After methyl 4-formylbenzoate had been completely consumed from the reaction solution, a 30% sodium hydroxide aqueous solution was added to the reaction solution so that the pH of the solution was adjusted to 7.5-8.0 while performing vigorous stirring at a stirring rate of 1300 rpm, followed by filtering the solution. Drying was performed at 80° C. under atmospheric pressure for 4 hr, affording 962 g (yield 99.5%) of methyl 4-hydroxyiminomethylbenzoate having 99.0% purity.

80 g of methyl 4-hydroxyiminomethylbenzoate obtained as above and 800 g of water were placed in an autoclave. 32 g of sodium hydroxide was added thereto and then thoroughly dissolved using stirring. The resulting solution was added with 6 g of 5 wt % Pd/C (wet 50% water), and was stirred for 4 hr while being heated to 45° C. under a hydrogen pressure of 10 kg/cm$^2$. After completion of the reaction, the reaction solution was cooled to room temperature and filtered to remove the catalyst.

The filtered solution was slowly added with 10% hydrochloric acid aqueous solution so that the pH thereof was adjusted to 4.5. The produced solid was filtered, recrystallized using a solution of methanol/water=1/1, and dried at 11° C. under atmospheric pressure, thus obtaining 52.7 g (yield 62.9%) of 4-aminomethylbenzoic acid hydrochloride having 99.9% purity as a white solid. As such, the melting point was 282-285° C.

Example 3

886 g of methyl 4-formylbenzoate having 99.0% purity obtained in Preparative Example 1 was dissolved in 2000 g of methanol, after which reactants of 450 g (6.47 mole) of hydroxylamine hydrochloride in 650 g of water was added thereto and the reaction mixture was stirred at a stirring rate of 800 rpm at 25-35° C. for 2 hr. After methyl 4-formylbenzoate had been completely consumed from the reaction solution, a 30% sodium hydroxide aqueous solution was added to the reaction solution so that the pH of the solution was adjusted to 7.5-8.0 while performing vigorous stirring at a stirring rate of 1300 rpm, followed by filtering the solution. Drying was performed at 80° C. under atmospheric pressure for 4 hr, affording 962 g (yield 99.5%) of methyl 4-hydroxyiminomethylbenzoate having 99.0% purity.

310 g of methyl 4-hydroxyiminomethylbenzoate obtained as above, 3000 g of water, 168.5 g of sodium hydroxide and 22.5 g of 5 wt % Pd/C (wet 50% water) were placed in a 4 L autoclave, and the reaction was carried out under conditions of a hydrogen pressure of 10 kg/cm$^2$, room temperature, a stirring rate of 1500 rpm, and a time of 3.5 hr. After the catalyst was removed, 452 g of conc. hydrochloric acid was added so that the solution was neutralized to pH 7, and water was then removed to concentrate the solution.

The concentrated solution was then filtered and dried, thus obtaining 4-aminomethylbenzoic acid.

Example 4 and Comparative Examples 1 and 2

These examples were performed in the same manner as in Example 3, with the exception that the stirring rate was changed to 2000 rpm, 700 rpm, and 1000 rpm, and the stirring time was changed to 3.5 hr, 2.5 hr, and 8.5 hr.

The results for different stirring rates and times are shown in Table 1 below.

TABLE 1

Effects of Stirring Rate and Stirring Time on Preparing AMBA

| | Reactor | rpm | Time (h) | MHB (%)* | HBA (%)* | Dimer (%)* | Others (%)* | AMBA (%)* |
|---|---|---|---|---|---|---|---|---|
| Ex. 1 | 4 L | 1500 | 3.0 | 0.0 | 3.4 | 1.2 | 1.9 | 93.5 |
| Ex. 3 | 4 L | 1500 | 3.5 | 0.0 | 0.0 | 1.7 | 2.6 | 95.7 |
| Ex. 4 | 4 L | 2000 | 3.5 | 0.0 | 0.0 | 1.6 | 2.8 | 95.6 |
| C. Ex. 1 | 4 L | 700 | 2.5 | 0.0 | 99.8 | 0.0 | 0.0 | 0.2 |
| C. Ex. 2 | 4 L | 1000 | 8.5 | 0.0 | 62.7 | 2.0 | 3.5 | 31.8 |

*LC (Liquid Chromatography) area %

As shown in Comparative Examples 1 and 2 and Examples 1, 3 and 4, the stirring rate and the stifling time had an effect on the reaction conversion to 4-aminomethylbenzoic acid. In Comparative Example 1 in which the stirring rate was the lowest and thus the area of contact between hydrogen gas and the reaction solution was small, MHB was converted into HBA but the conversion to AMBA was very low. In Comparative Example 2, the reaction time and the stirring rate were increased, and thus the AMBA reaction route was MHB→HBA→AMBA. However, the conversion to AMBA was much lower compared to Examples 1, 3 and 4.

As the stirring rate was increased as in Examples 1, 3 and 4, the conversion to AMBA was increased as is apparent from Table 1.

Example 5

886 g of methyl 4-formylbenzoate having 99.0% purity obtained in Preparative Example 1 was dissolved in 2000 g of methanol, after which reactants of 450 g (6.47 mole) of hydroxylamine hydrochloride in 650 g of water was added thereto and the reaction mixture was stirred at a stirring rate of 800 rpm at 25-35° C. for 2 hr. After methyl 4-formylbenzoate had been completely consumed from the reaction solution, a 30% sodium hydroxide aqueous solution was added to the reaction solution so that the pH of the solution was adjusted to 7.5-8.0 while performing vigorous stirring at a stirring rate of 1300 rpm, followed by filtering the solution. Drying was performed at 80° C. at atmospheric pressure for 4 hr, affording 962 g (yield 99.5%) of methyl 4-hydroxyiminomethylbenzoate with 99.0% purity.

62 g of methyl 4-hydroxyiminomethylbenzoate obtained as above, 600 g of water, 55.4 g (4.0 eq) of sodium hydroxide and 4.5 g of 5 wt % Pd/C (wet 50% water) were placed in a 1 L autoclave, and the reaction was carried out under conditions of a hydrogen pressure of 10 kg/cm², room temperature, a stirring rate of 1500 rpm, and a time of 3.5 hr. After the catalyst was removed, 145.2 g of conc. hydrochloric acid was added so that the solution was neutralized to pH 7, and water was then removed to concentrate the solution. The concentrated solution was then filtered and dried, thus obtaining 4-aminomethylbenzoic acid.

Examples 6-8

These examples were performed in the same manner as in Example 5, with the exception that the amount of NaOH added was changed to 48.5 g (3.5 eq), 33.7 g (2.4 eq), and 41.6 g (3.0 eq).

The different results relative to the amount of added NaOH are given in Table 2 below.

TABLE 2

Effects of Amount of NaOH on Preparing AMBA

| | Water (g) | MHB (g) | NaOH (g) | 5 wt % Pd/C (g) | Pressure (kg/cm²) | Composition (LC %) | | | |
|---|---|---|---|---|---|---|---|---|---|
| | | | | | | AMBA | Dimer | HBA | MHB |
| Ex. 5 | 600 | 62 | 55.4 | 4.5 | 10 | 95.1 | 1.2 | 1.1 | 0 |
| Ex. 6 | 600 | 62 | 48.5 | 4.5 | 10 | 95.8 | 1.5 | 1.6 | 0 |
| Ex. 7 | 600 | 62 | 33.7 | 4.5 | 10 | 92.0 | 1.8 | 3.9 | 0 |
| Ex. 8 | 600 | 62 | 41.6 | 4.5 | 10 | 93.5 | 1.2 | 3.4 | 0 |

As is apparent from Table 2, as the amount of NaOH was increased, the dimer by-product was produced in a smaller amount. Also, when NaOH was added in excess, the amount of the dimer was decreased but the amount of impurities was increased and the amount of AMBA was decreased. Also when NaOH was added in an amount about 0.8 times the weight of MHB, the yield of AMBA was the highest.

Example 9

886 g of methyl 4-formylbenzoate having 99.0% purity obtained in Preparative Example 1 was dissolved in 2000 g of methanol, after which reactants of 450 g (6.47 mole) of hydroxylamine hydrochloride in 650 g of water was added thereto and the reaction mixture was stirred at a stirring rate of 800 rpm at 25-35° C. for 2 hr. After methyl 4-formylbenzoate had been completely consumed from the reaction solution, a 30% sodium hydroxide aqueous solution was added to the reaction solution to adjust the pH of the solution to 7.5-8.0 while performing vigorous stirring at a stirring rate of 1300 rpm, followed by filtering the solution. Drying was performed at 80° C. at atmospheric pressure for 4 hr, affording 962 g (yield 99.5%) of methyl 4-hydroxyiminomethylbenzoate having 99.0% purity.

62 g (15 wt %) of methyl 4-hydroxyiminomethylbenzoate obtained as above, 320 g of water, 33.7 g (2.4 eq) of sodium hydroxide and 4.5 g of 5 wt % Pd/C (wet 50% water) were placed in a 1 L autoclave, and the reaction was carried out under conditions of a hydrogen pressure of 10 kg/cm², room temperature, a stirring rate of 1500 rpm, and a time of 3.5 hr. After the catalyst was removed, 89.1 g of conc. hydrochloric acid was added so that the solution was neutralized to pH 7, and water was then removed to concentrate the solution.

The concentrated solution was then filtered and dried, thus obtaining 4-aminomethylbenzoic acid.

Comparative Example 3

In order to evaluate the effect that the amount of MHB had, this example was performed in the same manner as in Example 7, with the exception that the amount of water was adjusted, so that the concentration of MHB was controlled to 20 wt % based on the total mass of the reactants.

The different results relative to the concentration of MHB are given in Table 3 below.

TABLE 3

Effects of Concentration of MHB on Preparing AMBA

| | Water (g) | MHB (g) | NaOH (g) | 5 wt % Pd/C (g) | Pressure (kg/cm$^2$) | Composition (LC %) | | | |
|---|---|---|---|---|---|---|---|---|---|
| | | | | | | AMBA | Dimer | HBA | MHB |
| Ex. 7 | 600 | 62 (9 wt %) | 33.7 (2.4 eq) | 4.5 | 10 | 92.0 | 1.8 | 3.9 | 0 |
| Ex. 9 | 320 | 62 (15 wt %) | 33.7 (2.4 eq) | 4.5 | 10 | 92.3 | 1.0 | 4.8 | 0 |
| C. Ex. 3 | 215 | 62 (20 wt %) | 33.7 (2.4 eq) | 4.5 | 10 | 3.8 | 0.2 | 95.3 | 0.2 |

As is apparent from Table 3, the AMBA conversion decreased in proportion to the increase in the concentration of MHB. Also when the concentration of MHB was low, the amount of final AMBA was lower. In Examples 7 and 9 in which the concentration of MHB was about 9 and 15 wt %, the amount of AMBA was high and the conversion to AMBA was also high. In Example 9 the efficiency of working volume is increased due to the use of a small amount of water, whereas in Comparative Example 3, when the concentration of MHB was too high, hydrogen solubility was decreased, and thus the reaction did not take place.

Example 10

886 g of methyl 4-formylbenzoate having 99.0% purity obtained in Preparative Example 1 was dissolved in 2000 g of methanol, after which reactants of 450 g (6.47 mole) of hydroxylamine hydrochloride in 650 g of water was added thereto and the reaction mixture was stirred at a stirring rate of 800 rpm at 25-35° C. for 2 hr. After methyl 4-formylbenzoate had been completely consumed from the reaction solution, a 30% sodium hydroxide aqueous solution was added to the reaction solution so that the pH of the solution was adjusted to 7.5-8.0 while performing vigorous stirring at a stirring rate of 1300 rpm, followed by filtering the solution. Drying was performed at 80° C. under atmospheric pressure for 4 hr, affording 962 g (yield 99.5%) of methyl 4-hydroxyiminomethylbenzoate having 99.0% purity.

6.2 g of methyl 4-hydroxyiminomethylbenzoate obtained as above, 60 g of water, 4.85 g (3.5 eq) of sodium hydroxide and 0.45 g of 5 wt % Pd/C (wet 50% water) were placed in a 100 mL autoclave, and the reaction was carried out under conditions of a hydrogen pressure of 10 kg/cm$^2$, room temperature, a stifling rate of 1500 rpm, and a time of 3.5 hr. After the catalyst was removed, 1.8 g of conc. hydrochloric acid was added so that the solution was neutralized to pH 7, and water was then removed to concentrate the solution.

The concentrated solution was then filtered and dried, thus obtaining 4-aminomethylbenzoic acid.

Comparative Examples 4 and 5

These examples were performed in the same manner as in Example 10, with the exception that KOH and Na$_2$CO$_3$ were used as the alkali.

The results for different alkalis are given in Table 4 below.

TABLE 4

Effects of Kind of Alkali on Preparing AMBA

| | MHB | | | | | Composition (LC %) | | | |
|---|---|---|---|---|---|---|---|---|---|
| | Water (g) | (g) | Kind of Alkali | Pd/C (g) | Pressure (kg/cm$^2$) | AMBA | Dimer | HBA | MHB |
| Ex. 10 | 60 | 6.2 | NaOH (g) 4.85 (3.5 eq) | 0.45 | 10 | 95.8 | 1.5 | 1.1 | 0 |
| C. Ex. 4 | 60 | 6.2 | KOH (g) 6.80 (3.5 eq) | 0.45 | 10 | 87.3 | 0 | 7.3 | 0 |
| C. Ex. 5 | 210 | 6.2 | Na$_2$CO$_3$ (g) 12.8 (3.5 eq) | 0.45 | 10 | 72.9 | 0 | 1.6 | 0 |

As is apparent from Table 4, the conversion of MHB to AMBA was different depending on the kind of alkali used in the process of making 4-aminomethylbenzoic acid. More concretely, when using KOH and Na$_2$CO$_3$ as the alkali, the yield of AMBA was not higher compared to when using NaOH. Thus, NaOH is particularly useful.

Although the embodiments of the present invention have been disclosed for illustrative purposes, those skilled in the art will appreciate that a variety of different variations and modifications are possible, without departing from the scope and spirit of the invention as disclosed in the accompanying claims.

Accordingly, such variations and modifications should also be understood as falling within the scope of the present invention.

The invention claimed is:

1. A method of preparing 4-aminomethylbenzoic acid, comprising:
   preparing methyl 4-formylbenzoate;
   reacting the methyl 4-formylbenzoate with hydroxylamine, thus producing methyl 4-hydroxyiminomethylbenzoate; and
   subjecting the methyl 4-hydroxyiminomethylbenzoate to catalytic reduction using hydrogen in a sodium hydroxide aqueous solution, wherein the catalytic reduction is performed at a stirring rate of at least 1200 rpm.

2. The method of claim 1, wherein the catalytic reduction is performed using a catalyst.

3. The method of claim 2, wherein the catalyst includes any one selected from among palladium, platinum, rhodium, iridium, and nickel.

4. The method of claim 2, wherein the catalyst is a Pd/C catalyst in which an amount of Pd is 1-15 wt % based on a total weight of the catalyst.

5. The method of claim 1, wherein the catalytic reduction is performed at a pressure of 1-15 atm and at a temperature of 30-50° C.

6. The method of claim 1, further comprising concentrating and filtering a product, after carrying out the catalytic reduction.

7. The method of claim 1, wherein the stirring rate is 1200-2000 rpm.

8. The method of claim 1, wherein the methyl 4-formylbenzoate is contained in an amount of 8-18 wt % based on a total weight of reactants.

9. The method of claim 1, wherein the sodium hydroxide aqueous solution is added in an amount 0.2-1.0 times a weight of the methyl 4-hydroxyiminomethylbenzoate.

* * * * *